United States Patent [19]

Traina

[11] Patent Number: 4,577,963
[45] Date of Patent: Mar. 25, 1986

[54] APPARATUS TO EVALUATE OBJECTIVELY THE CONCENTRATION AND MOTILITY OF PARTICLES SUSPENDED IN A SAMPLE OF LIQUID WITH DATA PROCESSOR AND DISPLAY OF THE RESULTS

[76] Inventor: Vincenzo Traina, Via A. De Ferraris, 18/D - Bari, Italy, 70124

[21] Appl. No.: 547,394

[22] Filed: Oct. 31, 1983

[51] Int. Cl.$^4$ ............................................. G01P 3/36
[52] U.S. Cl. ............................... 356/28.5; 356/434; 356/436; 356/440; 356/442
[58] Field of Search ................. 356/28.5, 434, 436, 356/440, 442

[56] References Cited

U.S. PATENT DOCUMENTS 3,825,346  7/1974  Rizzo .................................. 356/28.5
3,880,526  4/1975  Kobayashi et al. ................. 356/442
4,023,909  5/1977  Ross .................................... 356/434

Primary Examiner—S. C. Buczinski
Attorney, Agent, or Firm—Jacobs & Jacobs

[57] ABSTRACT

An apparatus to evaluate objectively the concentration and motility of particles suspended in a sample of liquid, and particularly to an apparatus to solve objectively the problem of evaluating these important characteristics in a very simple manner and in a short time by exploiting the Doppler effect. The sample to be examined is subjected to one of the two sub-beams resulting from the suitable division of a coherent monochromatic light beam emitted by a polarized LASER, while the other sub-beam is considered as a reference light sub-beam. Because of the very little difference between the frequencies of the original and scattered light a beat is originated in the rejoined two sub-beams which is dependent on the characteristics of the examined sample. Electromechanical means are provided to position automatically and sequentially a set of test-pieces to be examined according to a program and a data processor is provided to process the output signal of the rejoined sub-beams, so that the desired evaluations are displayed on a monitor or printed as alpha-numerical results and/or graphic diagrams. All of the mechanical, electromechanical, optical and data processor members are enclosed within a single box-container as component members of the apparatus.

7 Claims, 12 Drawing Figures

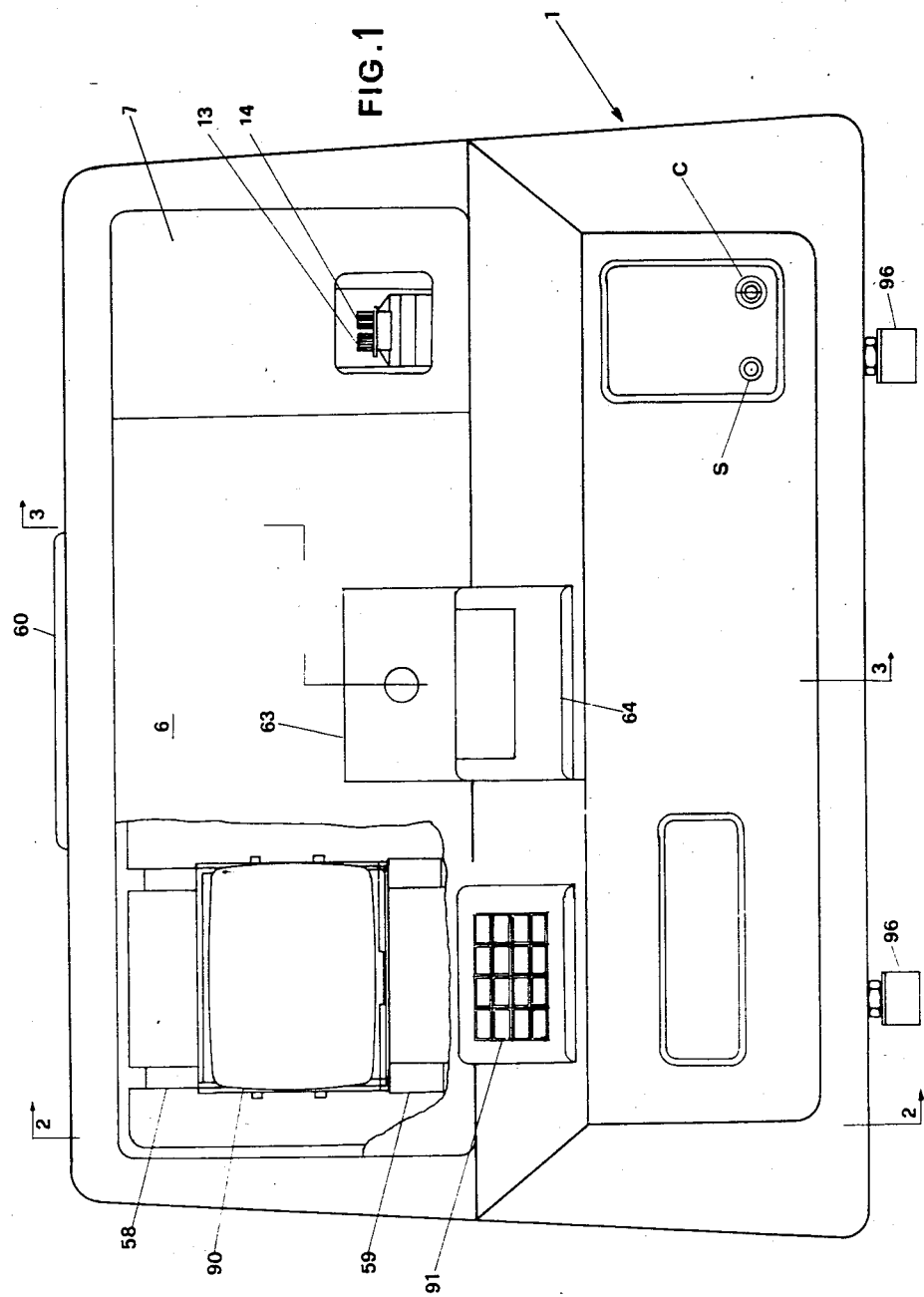

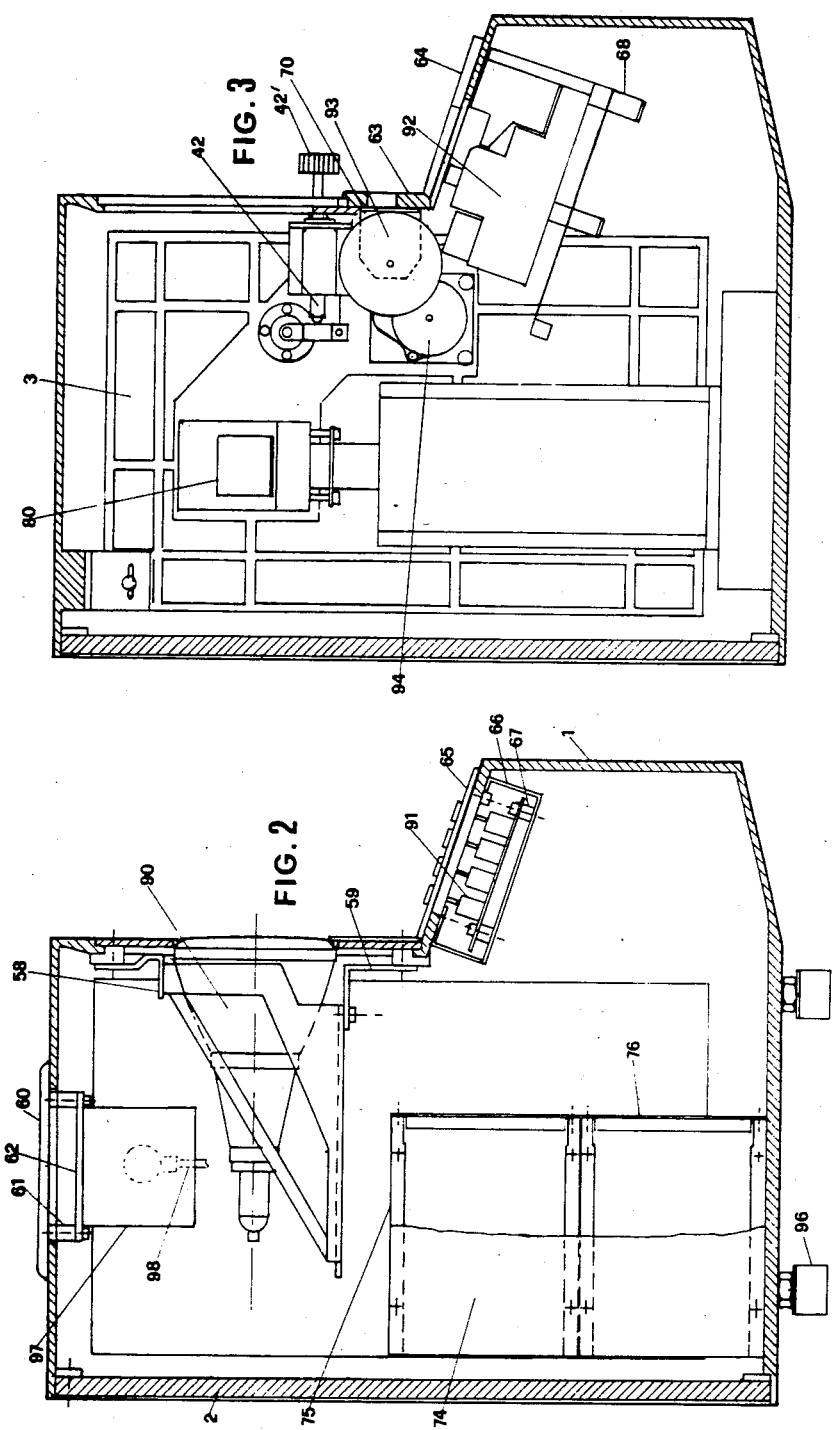

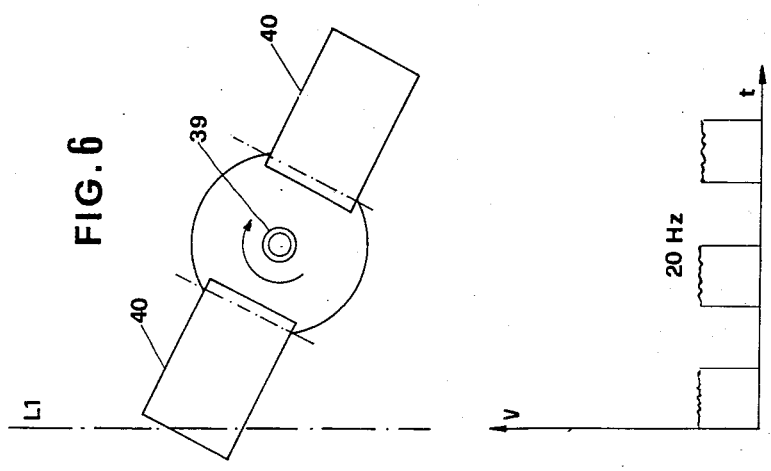
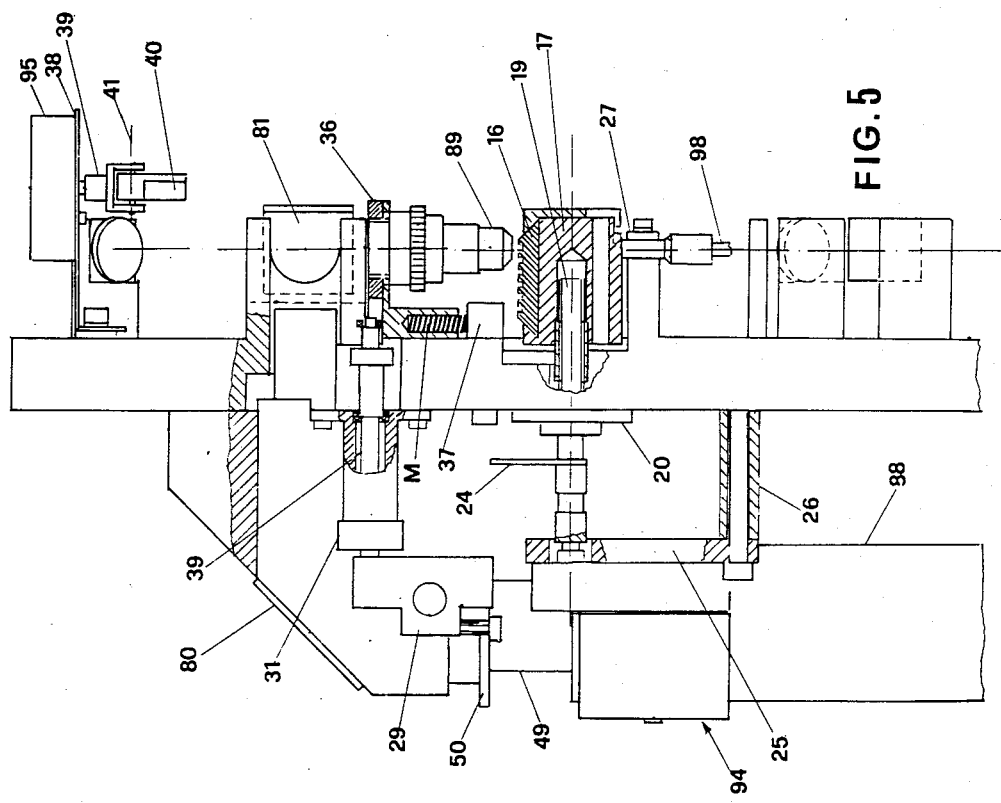

APPARATUS TO EVALUATE OBJECTIVELY THE CONCENTRATION AND MOTILITY OF PARTICLES SUSPENDED IN A SAMPLE OF LIQUID WITH DATA PROCESSOR AND DISPLAY OF THE RESULTS

The invention relates to an apparatus for evaluating objectively the concentration and motility of particles suspended in a sample of liquid, and particularly to an apparatus to solve objectively the problem of evaluating these important characteristics in a very simple manner and in a short time by exploiting the Doppler effect. The sample to be examined is subjected to one of the two sub-beams resulting from the suitable division of a coherent monochromatic light beam emitted by a polarized LASER, while the other sub-beam is considered as a reference light sub-beam. The division as well as the rejoining of the two sub-beams is carried out by using a suitable optical system, so that the beat of the two electromagnetic waves resulting from the very little difference between the original frequency of the reference sub-beam and the frequency of the examined sample provides an output signal to be detected and amplified by a first component member of an electronic system, so that the process of the data resulting from the sample examination is started. The alpha-numerical results are then displayed and/or graphically shown on a monitor and may also be printed by means of a printing device. This latter as well as the data processor and the monitor and the printing device are component members of the apparatus enclosed within a single box-container together with the optical system and all of the other mechanical and electromechanical component members of the apparatus. Sets of test-pieces may be examined sequentially and positioned automatically according to a program. The simultaneous microscopic observation of each test-piece through a telecamera is further provided for, the component members of which are also enclosed within said box-container.

The examination of liquid samples to evaluate some important characteristits of particles suspended therein is of interest in many fields of application, such as industrial, agricultural, biological fields; and the most important characteristics are generally considered the concentration and velocity of these particles within an examined fluid sample. The examination may, for example, concern the metallic particles in lubricating oil, micro-organisms and/or particles in a sample of water as regards the drinkableness of same; while the particles velocity may, for example, be related to problems of decantation velocity or to study the kinetics of biological reactions, e.g. the velocity of particles suspended in a liquid.

At the present time the microscopic analysis is to be considered as negligible when an objective and reliable evaluation is desired, or it may be useful as an auxiliary, subjective means of observation to be carried out by a person really skilled in the art. In any case only subjective results of such an observation are possible, the precision of which is obviously to be excluded.

The analysis of fluid having solid particles suspended therein has has however been proposed, experimented and sometimes applied in objective manner in the last decennia, and the attention has been devoted particularly to the examination of samples by exploiting the Doppler effect. The results have furthermore been processed by data processors in order to deduce really objective evaluations.

Substantially, an incident light beam emitted by a suitable light source has been divided in two sub-beams, one of which is really incident onto a sample to be examined while the other is considered as a reference sub-beam having the original frequency Because of the characteristics of the sample, the light scattered from this latter has only a very near frequency in respect to that original frequency, so that a beat is provided in the rejoined sub-beams the output signal of which is detected and processed to deduce important characteristics of the sample.

On these grounds, physical methods has been suggested and experimented by searchers, doctors and technicians, so that in the technical literature are, for example, reported quotations of Jouannet et al (Andrologia, 9, 1977), Shimizu et al (Transactions of Biomedical Engineering, March 1977), Hallet et al (Biophysical Journal, 1978). In respect to former subjective methods of analysis, as for example the microphotography of Jannick et al, cinematography of Rotschild and "photokimography" of Castelholz, the results of the new physical methods are really much more important, particularly when the analysis relates to the frequency spectrum of the light scattered from a sample of liquid having solid particles suspended therein, when an incident light beam of predetermined constant power is provided thereon. The exploitation of the well known Doppler effect was in this case considered as very useful.

To evaluate the results of the examination, data processors have already been used, the drawbacks of which are however depending on the particularly great size of same and its manifold use. That is to say, data processor have been suggested which are manufactured to satisfactorily process the results of many types of analysis, and not to evaluate only the concentration and motility of particles suspended in a liquid. This consideration is for example confirmed by the device specified in German Pat. No. 2 709 399 (Göhlde) which concerns the evaluation of the characteristics of cells suspended in a liquid cell and pre-treated with chemical substances, the examination being suggested by means of fluorescent excitations. The examination of an optical cell provided with a particle solution is suggested in GB Patent No. 1 202 612 (Commissariat à l'Energie Atomique), such an observation being crried out by using a light beam emitted by a LASER and incident onto the sample, in order to evaluate the characteristics of the movable particles. Description and illustrations are not sufficiently identified to enable the invention to be carried out by a skilled person.

Among other things, the attention of searchers and technicians has been devoted to the objective evaluation of concentration and motility of particles suspended in a liquid, on the ground of generally accepted formula of the Doppler effect:

$$f - f_o = 2(v/c)f_o \cos \alpha \operatorname{sen}(\theta/2)$$

wherein:
f=frequency of the scattered light of a sample when is struck by an incident light beam;
$f_o$=frequency of the incident light;
c=velocity of the light;
v=velocity of movable particles;

θ = diffusion angle (i.e. the angle between the direction of the incident light and direction of scattered light);
α = angle between the outer bisectrix of θ and the direction of the velocity v of movable particles.

As it is well known, the beat is due to the very small difference between the frequency f of the scattered light and frequency $f_o$ of the incident light. At the present time no device or apparatus may be considered in keeping with the exigences of the analyzer and easily disposable for what concerns a simple and objective examination of samples. Furthermore, no data processor has been proposed and/or applied as a component member of such an apparatus or device, to process only the results of the examination and deduce the recalled important characteristics of concentration and motility of particles suspended in a liquid.

A first important object of the invention is to provide an apparatus for the sequential examination of one or more sets of test-pieces according to a predetermined program, by exploiting the Doppler effect. A polarized LASER is provided as a source to emit a coherent monochromatic light beam which is then divided in two sub-beams, so that one sub-beam is incident onto the test-piece being examined and consequently scattered by same, while the other is considered the original, direct reference sub-beam. This latter is then rejoined with the scattered sub-beam to provide a beating between the respective electromagnetic waves, because of the very small difference between the frequencies $f_o$ and f so that the exploitation of the Doppler effect is possible. The output signal of the rejoined beam of light is then processed by the data processor of the apparatus to evaluate objectively the concentration and motility of solid particles suspended in the examined test-piece.

Another important object of the invention is to provide this apparatus with a suitable optical system, a first component member of which receives and reflectes the light beam emitted by the LASER, while a divider provides the division of two sub-beams forming an incident light sub-beam which is acting on the test-piece and a reference light sub-beam to evidence the Doppler effect through the beat of the scattered and reference lights when these latter are rejoined as a single beam, the output signal of which is processed by the data processor of the apparatus.

A further object of the invention is to provide in the apparatus a sliding support of the test-pieces to be sequentially examined, as well as an electromechanical control device for the automatic consecutive sliding motion of that support, so that each test-piece of each set of samples may be examined according to a predetermined sequence.

Another object of the invention relates to the use of a polarized He—Ne LASER (red light) the emitted light beam of which is firstly reflected by a first component member of the optical system and then interrupted periodically by means of the revolving vanes of a motorized device, while the direct reference sub-beam coming out from the divider of the optical system is at once interrupted by a disk which is acted by a suitable electromagnet.

Another object of the invention is to provide sets of programming cards to define the operating phases of the apparatus. At the start of the operation a set of questions are addressed to the operator through a monitor, who replies by acting suitable keys of a keyboard in order to control the operating course in accordance with the desired finality.

A further object of the invention is to provide the apparatus not only with said monitor, but also with a printing device, so that the processed results of the examination are displayed visually on the former and printed by the latter as alpha-numerical results and/or graphic diagrams.

An important object of the invention is also to provide a single box-container to enclose therein: all the mechanical and electromechanical component members; all the components of the optical system; the Laser, as a source emitting the coherent monochromatic light beam; the component members of the monitor to visually display the initial questions addressed to the operator and then the results of the examination; the keyboard and printing device, as well as the programming cards and components of the data processor.

In order to better value the novel characteristics of the apparatus according to the present invention and deduce the many advantages deriving by the use of same, a preferred embodiment is described hereafter as an example referred to the accompanying drawings. That is to say, this embodiment is not a limitation of the possible applications, so that ch-anges and/or modifications may be suggested by the skilled in the art without departing from the novel characteristics which are recalled in the claims.

In the drawings:

FIG. 1 is a front elevation view of the apparatus in accordance with a preferred embodiment of the invention.

FIG. 2 is a sectional view along line 2—2 of FIG. 1.

FIG. 3 is a sectional view along line 3—3 of FIG. 1.

FIG. 5 is a detailed elevation view particularly referred to a microscopic system of observation comprising a telecamera and a special illuminator of the test-pieces, some other component members being also shown in a sectional view.

FIG. 6 is a schematic view of a device comprised in this apparatus for interrupting periodically the light beam emitted by the LASER, like periodicity being also provided for the light sub-beam which is striking onto the sample.

FIG. 7 is a diagrammatic view of the square wave obtained through said periodical interruption of the light incident on the sample.

Figure 4:
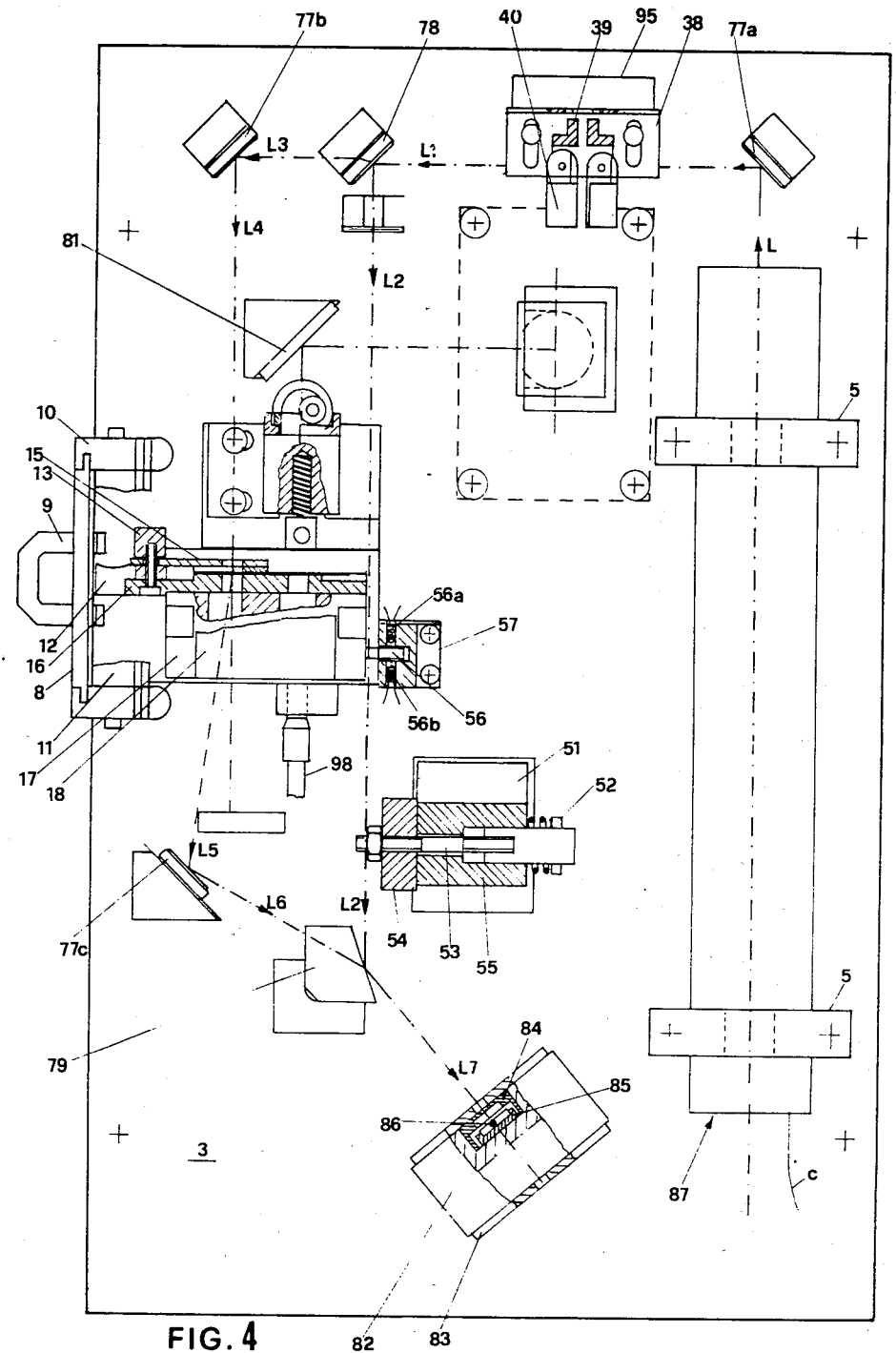
FIG. 4 is a schematic partially sectioned view of the main component members of the optical system and support of the test-pieces of a sample to be examined sequentially, the first component member of data processor being also shown in accordance with the invention.

Turning now to the drawings and first of all to FIGS. 1 to 3, the apparatus of this invention is shown as a box-container 1 with adjustable feet 96, the outward shape of which is lightly trapezoidal, and the projecting bottom part has a sloping upper surface. In turn, this latter evidences a keyboard 91 relating to the operating phases of a sample examination, and also a box-lid 63 and respective frame 64 relating to a printing device of the apparatus. On a monitor 90 are displayed not only the initial questions addressed to the operator for carrying out the examination of the selected test-pieces of a sample, but also the results of the examination after having been processed by the data processor of the apparatus. Furthermore, a microscopic observation is possible by a telecamera in order to follow the examination of each test-piece. Knobs 13, 14 are provided to set up these latter.

Through the schematic views of FIGS. 2 and 3 it is possible to understand that all the component members of the apparatus as well as the members provided for a microscopic observation, are housed within box-container 1 the backward side of which is closed by means of a closing member 2.

Some important novel features of the invention are schematically shown in FIG. 4. It is actually possible to see the supposed position and assembling of many component members of the appatus in accordance with the preferred embodiment, e.g.: all the component members of the optical system; the component members provided to suitably illuminate each test-piece during a sequential examination of same, so that the contemporaneous observation by a microscope with telecamera is possible because of the automatic sliding motion of the test-piece support according to a predetermined program of examination. A first component member of the provided data processor is also shown, to detect and amplify the output signal inflenced by the Doppler effect, the process being then continued by the other component members of the data processor. As a matter of fact, the apparatus according to the present invention allows all the phases of examination of samples, beginning from the emission of a coherent monochromatic light beam by a Laser, up to the display of alpha-numerical and/or diagramatic results on a monitor and/or on a printed board.

A LASER 87 is energized through conductors c to emit a coherent monochromatic light beam L which is reflected by a first component 77a of the optical system to form a reflected light beam L1. This latter is at once subjected to a division by a divider 78, so that a first reference sub-beam of reflected light L2 having the original frequency $f_o$ is coming out together with a second sub-beam of refracted light L4 which is directed and incident on such a test-piece of the sample which in turn is to be examined in that instant.

By carefully looking at schematic view of FIG. 4 it will be easily understood that a scattered light beam L5 is coming out from the test-piece and is dependent on the characteristics of the examined sample.

A sample-holder 16 is provided with grooves to house a set of test-pieces which are firmly retained therein and sequentially positioned because of the automatic predetermined sliding motion of a sample-holder support 17.

Reference sub-beam L2 is directed to a reflecting-refracting component member 78 of the optical system, while the scattered sub-beam L5 coming out from the test-piece is reflected by another reflecting member 77c as a sub-beam L6 and refracted by component member 79. In this manner a rejoined beam L7 is formed the beating phenomenon of which is generated by the two electromagnetic waves having the very near frequency $f_o$ of the reference sub-beam L2 and the frequency f of the scattered light L6, respectively. The output signal of L7 is finally detected by a photodetector 86, i.e. by the first component member 101 of the data processor 100 of the apparatus.

According to the schematic view of FIG. 4, the optical system comprises therefore reflecting mirrors and reflecting-refracting component members to provide the beating phenomenon as recalled hereabove. The physical method of sample examination may be considered as generally used at the present time, the purpose of which is principally to exploit the Doppler effect for deducing objectively the most important characteristics of the examined sample.

Some novel features of the invention are however to be pointed out which concern not only the optical system by itself, but also the influence of constructive and operating particularities of the appartus, the advantages of which are easily deducible by the skilled in the art.

To better understand the novel features of the invention it is first of all important to recall here that all the mechanical, optical, electronic component members of the apparatus, as well as those for the microscopic observation of a sample during the examination are housed within a box-container 1 the backward plane 2 of which is closed and removable for assembly, disassembly and maintenance operations.

Inside box-container 1 three main groups are provided, namely:

1. A group comprising nearly all mechanical and optical component members of the apparatus according this preferred embodiment of the invention, the optical component members (reflecting mirrors, divider, prism) being assembled adhesively on a suitable slab 3.

2. A card-holder 74, 75, 76 to hold at its inside nearly all the programming cards, excluded those relating to such operations which are to be provided by means of keyboard 91 and printing device 92.

3. A group comprising an illuminator 97, a monitor 90, a printing device 92 and a keyboard 91.

Apart from constructive feature of this preferred embodiment (e.g. the mechanical supports performed directly by suitably casting and working the slab 3, or said adhesively assembly of component members of the optical system on this latter), the attention of the skilled in the art is to be called to following features of the apparatus:

a. An electromagnet 55 and a synchronous motor 95 are provided with respective mechanisms in order that the reference light sub-beam L2 and reflected light beam L1 of the light beam L emitted by LASER 87 may be interrupted, the interruption of light beam L1 being however periodical, as it will be explained hereafter. That interruption has the purpose of examining the test-piece according to a novel technical manner which is very different and more advantageous in respect to the prior technique to evaluate the total number of the particles suspended in a liquid sample.

b. The apparatus according to the present invention allows to follow microscopically the course of the examination, a very different microscopic vision being provided not only because of the use of a telecamera, but also for what concerns the illumination, the vision on a monitor and the evaluations of the resulting data.

In FIGS. 2 to 5 the top side of box-container 1 is provided with an illuminator 97 supported by a plate 60 through spacers 61. The illuminator is, in turn, provided with a low tension halogen tube and a parabolic diffuser to concentrate the emitted light within an optical fibre 98 having a flexible sheath. Such optical fibre is fixed on slab 3 and the other end of same penetrates inside sample-holder support 17, so that the test-piece to be examined may be suitably illuminated when is positiond under the lens 89 of a microscope. On the other hand, this latter is slidable in order to be focalized, and a suitable lever system 29, 30 is provided for that purpoose. A set of reflecting mirrors 80, 81 are also provided for the proper utilization of a telecamera 88, so that the visual image displayed on monitor 90 evidence the movable particles of the sample magnified ×400. In this preferred embodiment a monitor of 6" is provided.

c. In accordance with the invention, a set of at least six test-pieces are placed in respective grooves of sample-holder 16. The test-pieces are in the form of mini-test tubes having a rectang-ular cross-section, one side being about 0.1 to 0.4 mm high, and the other about 1 to 3 mm wide, while a length of about 30 to 40 mm is preferred. In this manner the test-pieces lean substantially on a plane.

To carry out predetermined sequential examinations, such a set of test-pieces is placed and fastened in sample-holder 16 the support member of which 17 is automatically slided by means of an electromechanical system drive by a synchronous geared motor 94. A timed sliding motion of sample-holder 16 is then possible according to a programed sequence of examination which may be followed on monitor 90. A visual display on monitor 90 is also possible for any one of the test-pieces as desired by the operator when a suitable key of the keyboard 91 is acted.

As shown in FIG. 5, the motion of sample-holder support 17 is performed by means of a screw 19. This latter is solid for support 17 and rotated by said synchronous geared motor 94, the right angular position of which is obtained through a photoelectric cell energized by a feeler 24 which, in turn, helps forward the function of a set of emitters-detectors, two of which are shown in FIG. 4 with reference numerals 56a and 56b. These latter are assembled in a support member 57 together with their feeler 56, so that the six predetermined positions of sample-holder 16 may be exactly located.

By looking at FIG. 4 it is further possible to notice that a pair of supports 10 is provided, the specularly opposite grooved guides of which allows the sliding motion of a box-lid 8 by a handle 9 and then the admittance inside box-container 1 to place the sample-holder 16. Such a box-lid 8 is, in turn, supported by a panel 7.

d. The card-holder 74, 75 contains all those cards which have analog and digital functions. The cards are of a standard size. In accordance with this preferred embodiment of the invention they are placed in two superposed planes 74, 75 and the wire harness of same is performed by a printed circuit-master plate 76.

As premised, the main scope of the invention is to provide an apparatus to evaluate objectively the concentration and motility of particles suspended in a liquid sample. In accordance with this preferred embodiment the examination is carried out sequentially on at least six test-pieces and the results are processed by means of a data processor of the apparatus in order to be displayed on a monitor or printed by a printing device as alpha-numerical and/or digramatical results.

Figure 8:
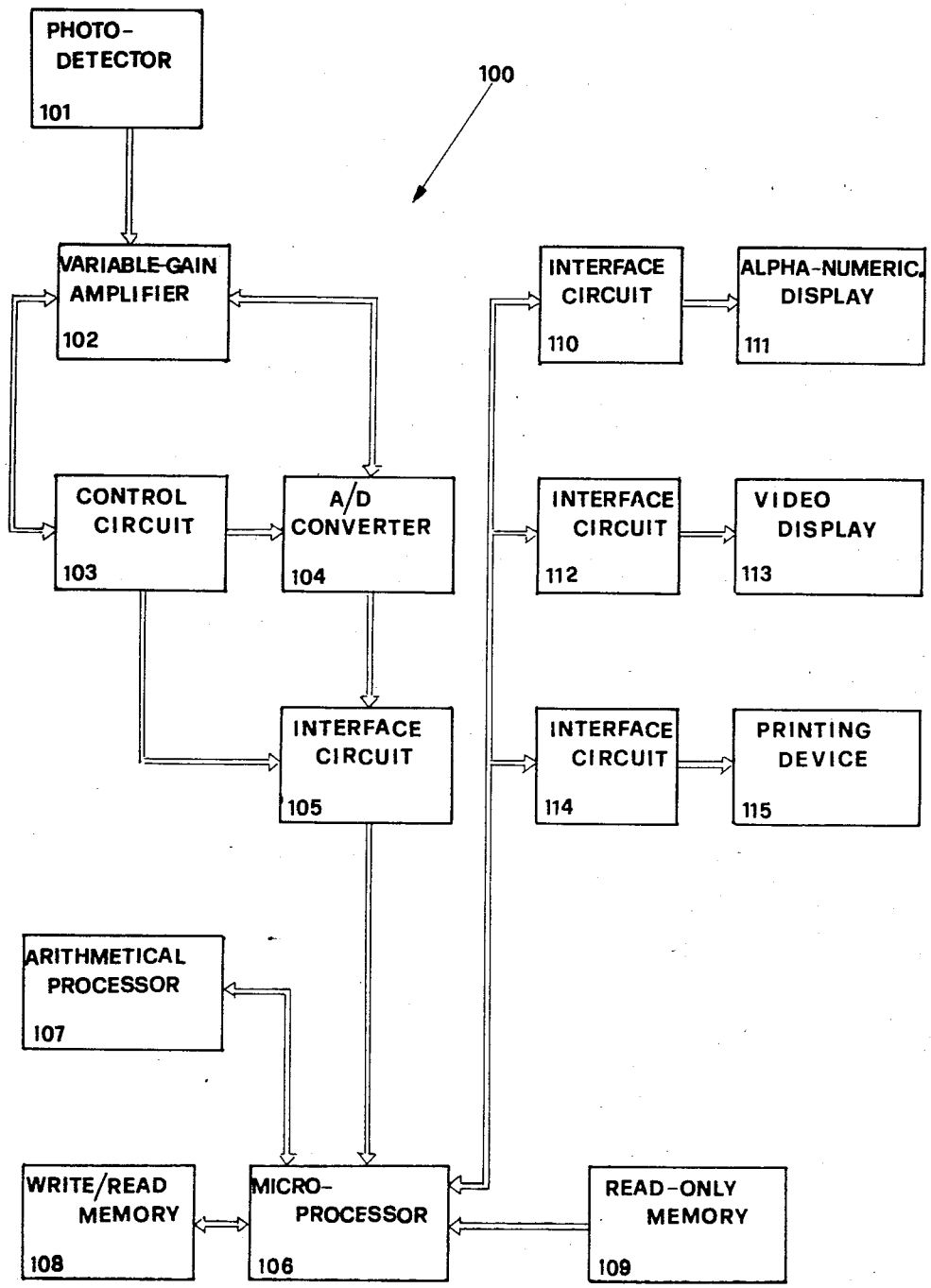
FIGS. 8 to 12 are the detailed circuits relating to the main component members of the electronic system in accordance with this preferred embodiment of the invention.

An electronic circuit system 100 of the data processor of the apparatus is schematically shown in FIGS. 8 to 12. FIG. 8 shows a block diagram while the other FIGS. 9 to 12 show the electronic circuits of the single components, the functions of which are better explained hereafter.

Figure 9:
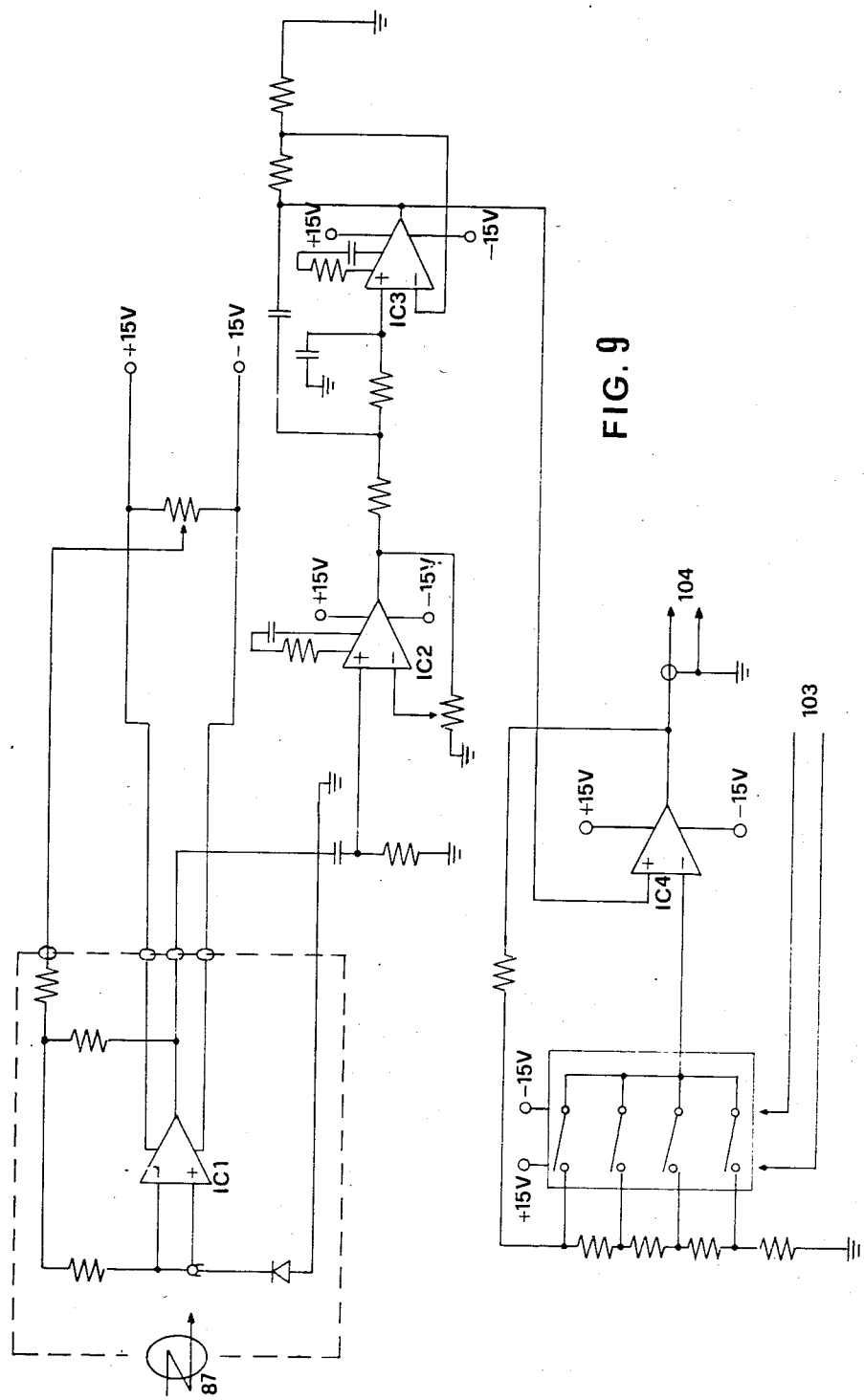

The first electronic component, indicated by reference numeral 101, is preferably assembled with the end part of the optical system of the apparatus. Component 101 is a photodetector the function of which is to detect and amplify the output signal of the rejoined light beam L7, and comprises a photodiode of PIN type and a pre-amplifier IC1. It is indeed to be recalled that both sub-beam of light L5 diffused by a sample after the light beam L emitted by LASER 87 has been divided, and the rejoined beam L7 are very faint. The use of a very sensitive photodiode of PIN type together with the next pre-amplifier IC1 permits to have a sufficient output voltage. As shown in FIG. 9, the output signal of pre-amplifier IC1 is furthermore amplified and filtered by a band-pass filter from 0.1 to 300 Hz, by means of integrated circuits IC2, IC3, so that any noise of pre-amplifier IC1 and photodiode PIN may be eliminated.

On the ground of many experiments of the Applicant it was possible to deduce that the analysis system must have a dynamics of at least 90 dB to abridge the variations of intensity which are eventually presented by a signal to be analyzed, when the examination is performed by passing from a pathologic to a normal sample; and the components indicated with reference numerals 102 and 104 in FIG. 8 allow to reach such a dynamics.

Component 104 is in effect an analog-to-digital converter of 11 bits+1 of sign, and using same a dynamics of $20 \log 2^{11} = 66$ dB is reached. The remainder 24 dB are added particularly when the signals are very faint, the amplification of same being provided by a variable-gain amplifier indicated with the reference numeral 102 in block-diagram of FIG. 8 and comprising the integrated circuit IC4. Such amplifier is programable by digital signals G0, G1 which, in turn, acts on component 103 as control circuit of the variable-gain amplifier 102, so that the regulation on the basis of said signals may be performed and the converter 104 may operate with its best dynamic characteristics.

Figure 10:
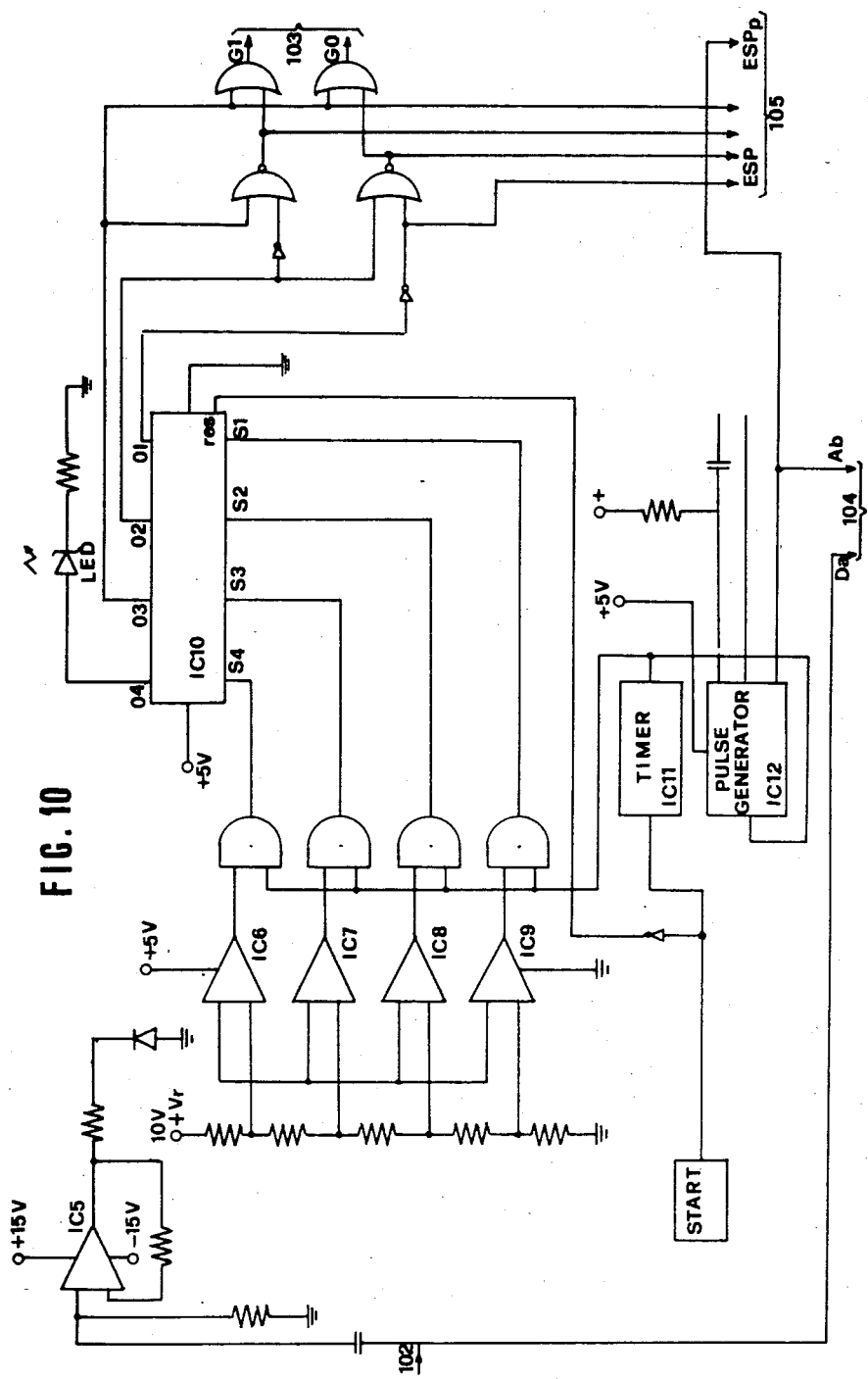

In circuit section of FIG. 10 it is possible to see that the signal coming out from above circuit section is fed to a four comparator unit having passed through a buffer IC5, this unit comprising the integrated circuits IC6, IC7, IC8, IC9 which have fixed levels of voltage.

To start the exponential analysis a respective key is provided in keyboard 91. The integrated circuit IC10 stores then the maximum intensity of the signal according to exponential values $1-2^1-2^2-2^3$ and overflow during the time of 10 seconds, controlled by a timer IC11, after which said signals G0, G1 are obtained by a suitable decodification. At the end of this stated time interval of 10 sec a pulse $ESP_p$ of 10 msec is generated by the integrated circuit IC12 to point out that the exponential signal has been computed.

Figure 11:
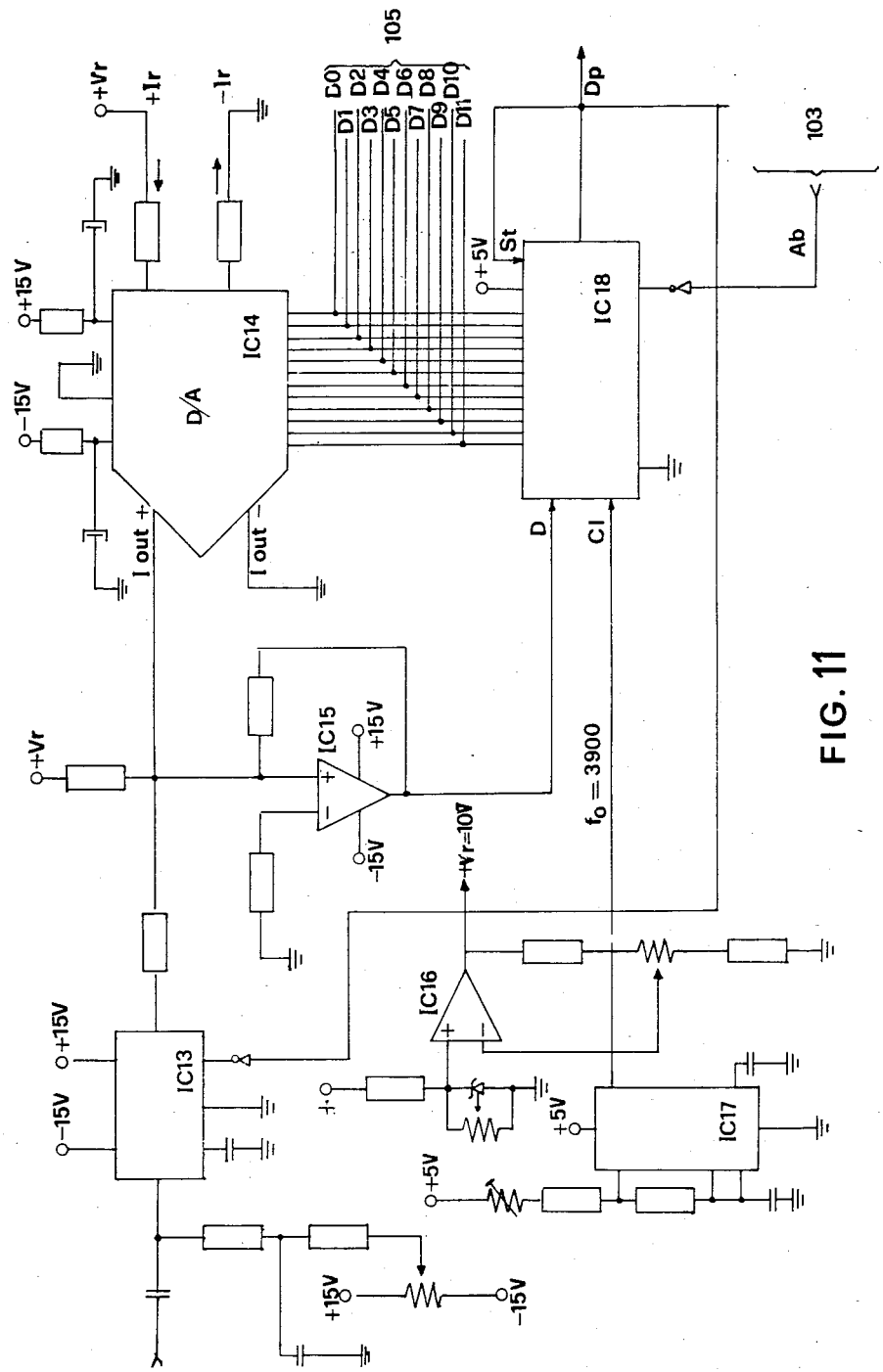

According to the detailed circuit of FIG. 11 the output signal of variable-gain amplifier 102—the middle value of which is 0 because of the effect of the band-pass filter—is added to a continuous component equal $V_r/2$, where $V_r$ is the predeterminad reference voltage of 10 V. Such compound signal will never have the value 0 or a voltage like the reference voltage $V_r$ because of the compression of variable-gain amplifier 102. Furthermore, from the detailed circuit of FIG. 11 it is possible to notice that the signal passes through an integrated circuit IC13 having sample-and-remember features and is then continuously compared with the output of a digital-to-analog converter of 12 bits by means of integrated circuit IC15. This converter comprises the integrated circuit IC14, while the output data D of integrated circuit IC15 is passed to the integrated circuit IC18 to form a register of 12 bits of the sequential approssimation type. When a result of equality is coming out through such a comparison, an output signal date of 12 bits is obtained together with a validation signal (Ready Date $D_p$) from the integrated circuit IC18, to be passed to interface circuit A/D indicated by the reference numeral 105.

As premised, the maximal frequency of the signal is 300 Hz. The sampling frequency will have a double value. From the detailed circuit of FIG. 11 it is also possible to notice that an oscillator IC17 is provided which is suitable to give a frequency $f_o=3,900$ Hz, i.e. equal to $13\times300$ Hz, where $13=12$ bits$+1$ (Ready Date $D_p$).

A special signal Ab from the control component 103 of the amplifier and exponential helds the analog-to-digital converter to be stopped at the output value 0 during the presentation time interval of 10 msec relating to the exponential.

Figure 12:
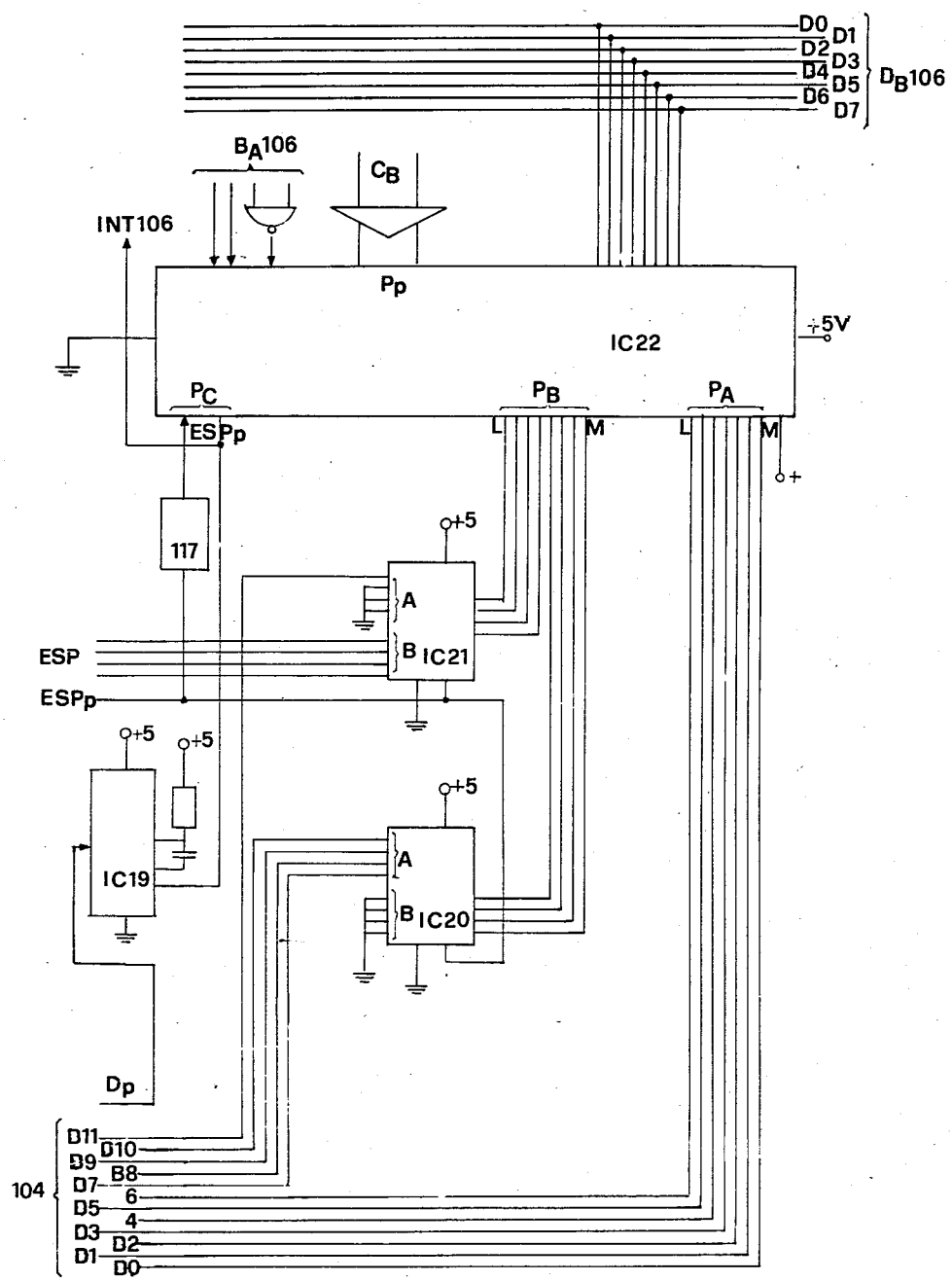

According to the detailed circuit of FIG. 12 the exponential of the signal converted to a digital data is successively presented to the low section of the gate $P_B$ of integrated circuit IC22, while the high section of gate $P_B$ is put to the value 0 through the integrated circuit IC20. The whole operation is carried out in the time interval of 10 msec of the Exponential Ready signal indicated with reference characters $ESP_P$. The data are successively presented to the gate A of integrated circuit IC22 and high section of gate B of same, together with a bit of the low section, i.e. a total of 13 bits (12 bits of the signal$+1$ bit high fixed), while the remainder is put to 0. An output pulse from integrated circuit IC19, the duration of which is 45 $\mu$sec, is directed to a microprocessor 106 (see FIG. 8) to advise that in analog-to-digital converter indicated by reference numeral 104, the date $D_p$ is ready, so that the operation is to be cut off.

From the detailed circuit of FIG. 12 it is further possible to deduce that the signal of the bus of data $D_B$ relating to the microprocessor 106, as well as those of control bus $C_B$ from the programable gate $P_p$ and addressing bus $B_A$ of processor are all conveyed to the integrated circuit IC22.

The operational continuation of electronic system 100 according to block diagram of FIG. 8 is substantially carried out in a conventional manner to display the results as stated above. Original data are then stored in a write/read memory RAM (Random-Access Memory) indicated by reference numeral 108. In accordance with this preferred embodiment of RAM is provided with two sets of 128 data, while three other free sets are utilized by the microprocessor 106 to process the data through the aid of an arithmetical processor 57 as soon as a first set of data $D_p$ is ready.

The program of the data acquirement, processing, storage and display is performed in a memory AFROM (Read-Only Memory) indicated by reference numeral 109. It may be important to notice that such memory has been provided with employment of $8K\times8$, wherein K is the measuring unit equal to 1024, as it is well known. The desired display of alpha-numerical and/or diagramatic results is then performed through the interfaces, in relation to one or more samples of solid particles suspended in a liquid. That is to say, the output signal of the rejoined beam L7 after the beating phenomenon has been evidenced is sent to the processor 100 and processed and displayed in a short time. An objective and reliable evaluation of the most important characteristics of the sample/samples is then deduced in a visual and/or printed form, in accordance with the basic principles of the present invention.

Turning now to the operation of the apparatus in accordance with a predetermined programming, following phases may be resumed:

I. Activation of the apparatus by means of a special key into lock C, the ON condition being indicated by a warning light S. Either lock C and warning light S are provided on the frontal panel of box-container 1, as shown in FIG. 1.

II. Visual display on monitor 90 of a question sequence to carry out a sample examination as desired. The questions are addressed to the operator who replies by acting the suitable keys of keyboard 91.

To better understand this important phase of the operation a supposed sequence of questions as well as a supposed sequence of replies are reported hereafter

| Questions | Replies |
|---|---|
| Date of the analysis ? | 05, 25, 1983 |
| Number of test-pieces ? | from 1 to 6 (e.g. 3) |
| Test-piece N.1 - Part No. ? | |
| Test-piece N.2 - Part No. ? | |
| Test-piece N.3 - Part No. ? | |
| Number of readings for each test-piece ? | from 1 to 6 (e.g. 4) |
| I reading | START |
| II reading | ? |
| III reading | ? |
| IV reading | ? |
| Initial time | ? |

The key START of keyboard 91 is to be pressed to START the operation.

It is then possible to program:
The number of test-pieces of each sample, to be examined sequentially (from 1 to 6 in accordance with this preferred embodiment)
The part number of each test-piece represented by a respective mini-test tube (e.g. a number of eight figures)
The number of examinations to be repeated for each set of test-pieces relating to a sample (e.g. from 1 to 6)
The time interval from beginning the examination of a set of test-pieces to the beginning of the next set
The initial time of the first set of examinations.

After the key START has been pressed, sample-holder 16 is automatically positioned to examine the first test-piece. The examination of test-piece No. 1 is then begun. At the end of this first examination, sample-holder 16 is automatically slided and rightly positioned because of the automatic sliding motion of its suport member 17, so that test-piece No. 2 is examined. The sequential examination of all the programmed test-pieces is carried on, a middle time of about 1 minute being sufficient to carry out the examination oof each test-piece.

As said above a time interval is programmed from beginning the examination of a set of test-pieces to the beginning of the next set. At the end of the examination of said first set of test-pieces the apparatus is then placed in a pause state, till the end of the programmed time interval. During such a pause state the operator may switch ON the illuminator 97 for a microscopic vision as well as to position the sample-holder as necessary in order that any desired test-piece may be visually observed on monitor 90.

At the end of the programmed pause the illuminator 97 is automatically switched OFF and sample-holder 16 is also automatically positioned to begin the examination of a new set of test-pieces.

As said above, the results are displayed visually on monitor 90 and/or printed by the printing device of the apparatus as definitive alpha-numerical evaluations and/or graphic diagrams.

At the end of each examination on monitor 90 are displayed:
a semi-log graphic histogram of the power spectrum;
middle velocity of the suspended particles in μm/sec;
total number of the suspended particles as number/cm$^3$;
total number of the motile particles as number/cm$^3$.

In accordance with the requirements of the operator, printing device 92 displaies said informations as alpha-numerical results relating to all the examinations already carried out till that moment. When requested by the operator printing device 92 may also display in a print form the histogram simultaneously of like display on monitor 90.

It is further important to notice that the printing display may be requested by the operator in any moment, as such a request is stored and then satisfied during a pause state of the apparatus. At the end of the cycles of the analysis it is furthermore possible to have a print of the results concerning all the programmed examinations. Besides the analysis results, all the data relating to same are displaied, namely: number of the sample; part number of the same; number of the examination; starting time of a set of examinations, etc.

For what concerns the operating technique in accordance with the invention is is important to point out that:
the evaluation of motility and total number of motile particles is obtained by the examination of the power spectrum in accordance with a known methodologie;
the evaluation of the total number of suspended particles in performed by a novel technique based on the test of intensity of the light scattered by the sample, independently from the frequency of same. Referring to the accompanying drawings and particularly to FIGS. 4 to 7, such a test may be resumed as follows:

Before the evaluation through the power spectrum (FFT-Fast Fourier Transform) the electromagnet 55 is energized and synchronous motor 95 is started, so that the disk 54 of the former interrupts the reference sub-beam L2 of Laser 87, while through the shaft of the latter a hub 39 is rotated which is provided with a pair of diametrally opposed vanes 40 hinged thereon. Because of the centrifugal force and aerodynamic action due to the suitable shape of the two vanes (aeodynamic lift) both vanes are moved angularly till a near horizontal plane, as better shown schematically in FIG. 6, so that the reflected light beam L1 of the coherent monochromatic light beam L emitted by the LASER 87 is periodically interrupted. When a velocity of 600 r/min is assumed for motor 95, i.e. 10 r/sec, 20 interruptions/sec of the light beam L1 are performed by the pair of vanes 40.

The light signal scattered by the sample is also interrupted 20 times/sec and the diode PIN 86 is after all emitting an electric signal at the frequency of 20 Hz, the wave shape of which is like that shown in FIG. 7. Such an electric signal is then processed by the analog-to-digital circuits of processor 100 to deduce the other important parameters; that is to say no other electronic circuit is to be added to carry out the process of the scattered light beam to define this type of test.

The continuous component of the signal is separated and its quadratic module is calculated to deduce the signal power; this latter value is then carried to a middle quantity in the time of 30 sec to reach steady values. It is also to notice that the value deduced in this manner is proportional to the total number of particles which are running over by the incident sub-beam L4. Furthermore, the previous setting of the apparatus allows to fix the value of the constant of proportionality and display the results as the concentration of the particles suspended in a liquid sample.

It will be understood that this process may be used in many cases wherein the evaluation of concentration and motility of particles suspended in a liquid is important, as it was remarked preliminarily.

A particular importance is to be attached to the test of concentration in following cases:

1a—Metal particles suspended in lubricating oil to solve the problems of evaluation relating to mechanical and lubricating wear.

1b—Inorganic particles (e.g.silica) suspended in water to be used for industrial and/or feeding purposes.

1c—Solid particles suspended in a washing water to verify the saturation.

1d—Organic and/or inorganic solid particles suspended in natural or artificial watercourses to evaluate the pollution state of same.

1e—Concentration of solid particles in liquid samples upstream or downstream a filter, filter press, decantation system, in order to evaluate the filtering effectiveness and the necessity of regenerating the filters.

1f—Concentration of microorganisms and/or other particles suspended in fluids for analysis of the biological type, e.g. relating to water potability, fluid cultivation beds, blood particles (red corpuscles), urine particles (leucocytes, flaking of cells, etc.).

For what concerns the velocity of solid particles suspended in a liquid, a particular importance is to be attached, for example, to the following cases:

2a—Problems of decantation by taking into account that: the velocity is a function of many parameters, e.g. specific weight of the fluid and solid; viscosity; surface tension; size and shape of the particles; temperature, etc. and cannot be provided for by theoretical formulae; industrial applications which are, for example, relating to the decantation, water clarification, chemical lowering of the hardness of industrial water, etc.

2b—Evaluation of the motility of microorganisms in biological solutions on the basis of environmental conditions (temperature, pH, presence or not of inhibitory or stimulating chemical substances).

2c—Evaluation of the kinetics of biological reactions depending on the velocity of the particles contained in certain solutions, for example the sedimentation and coagulation velocity of the blood, also in relation to the rate of heparine or some other coagulant.

I claim:

1. An apparatus to evaluate objectively the concentration and motility of particles suspended in a liquid sample/samples examined sequentially by exploiting the Doppler effect, such apparatus comprising:
a box-container (1) wherein all the mechanical, electromechanical, optical component members as well as the component members of a data processor (100) are enclosed to examine sequentially one or more test-pieces and process the respective results;
a polarized LASER (87) energized through conductors (c) to emit a coherent monochromatic light beam (L) which is reflected, divided and/or refracted by means of a suitable optical system; in order that the favourable conditions for exploiting the Doppler effect may be realized;

an optical system comprising reflecting members (77a, 77b, 77c), a divider (78) and a prism (79), so that the firstly reflected light beam (L1) is divided in two sub-beams (L2, L4), the former being a reference sub-beam (L2) the frequency of which is like the frequency ($f_o$) of the original beam (L) emitted by the LASER, while the latter is the sub-beam incident on the examining test-piece and influenced by the characteristics of same, so that a scattered light sub-beam (L5) is provided having a very near frequency (f) which is rejoined with reference sub-beam (L2) to finally provide a single rejoined beam (L7) the output signal of which is detected and amplifier by a photodetector (101) and processed by the data processor of the apparatus;

an electromechanical system to support and move a sample-holder (16) which is provided with a set of grooves to seat a respective set of test-pieces, the support (17) of sample-holder (16) being driven by a synchronous gear motor (94) in order that the test-pieces may be sequentially and automatically positioned for the examination in accordance with a previously programmed motion of support (17) and term of each examination through programming cards housed in a suitable card-holder (74, 75, 76) of box-container (1);

a data processor (100) to process and display the final results as alpha-numerical evaluations and/or graphic diagrams;

a monitor (90) to visually display the results;

a printing device (92) to display in a print form the results, either as singly referred to each test-piece and/or on the whole;

a keyboard (91) the keys of which are acted by the operator to carry out the operative phases of a sample examination.

2. An apparatus as claimed in claim 1 wherein:

the timed sliding motion of sample-holder support (17) is performed by a synchronous gear motor (94) so that a selected test-piece to be examined or microscopically observed is automatically positioned in its right position by the help of a set of emitters-detectors (56a, 56b ...) which are acting with a feeler (56);

a synchronous gear motor (94) is provided for that right positioning of selected test-piece to be examined;

a photocell energized by another feeler (24) is also provided to make sure of such a right positioning of the test-piece, the whole being depending on the electronic system (100) of the apparatus.

3. An apparatus as claimed in claim 1 comprising:

an illuminator (97) provided with a low tension halogen tube and a parabolic diffuser to concentrate the light within an optical fiber (98) and direct same on the sample which is to be illuminated for the examination;

an electromagnet (55) with a coaxial disk (54) to be slided for interrupting automatically the reference light sub-beam (L2);

a motor (95) to rotate a hub (39) and a pair of diametrally opposed vanes (40) hinged thereon, in order that these latter may interrupt the reflected beam (L1) simultaneosly to said interruption of reference light sub-beam (L2) and a final periodical interruption of the scattered light beam of the sample is provided.

4. An apparatus as claimed in claim 3 wherein the scattered luminous signal coming out from the sample is interrupted 20 times/sec and is after all detected and amplified as an electric signal by a photodetector (101) having a square wave frequency of 20 Hz which is to be processed by processor (100).

5. An apparatus as claimed in claim 1 wherein at the start of the operation a set of questions relating to the phases of the examination is put to the operator displaying same on monitor (90), the answers being defined by this latter through the action on suitable keys of keyboard (91), so that the sequence of the operation phases is performed automatically.

6. An apparatus as claimed in claim 1 comprising a data processor (100) to process the results of the examination of particles suspended in liquid samples and display same as alpha-numerical evaluations and/or graphic diagrams on said monitor (90) or in a print form through a printing device (92) either as singly referred to the test-piece of a sample and/or as a whole.

7. An apparatus as claimed in claim 1 comprising a microscope (89) with telecamera (88) for a microscopical observat on of test-pieces, during the operation, the microscopic image of any one of the test-pieces being further displayed on monitor (90) as desired and suitably controlled by the operator.

* * * * *